(12) United States Patent
Hendrickson et al.

(10) Patent No.: US 11,555,185 B2
(45) Date of Patent: Jan. 17, 2023

(54) TARGET ENRICHMENT

(71) Applicant: New England Biolabs, Inc., Ipswich, MA (US)

(72) Inventors: Cynthia Hendrickson, Wenham, MA (US); Sarah Bowman, Ipswich, MA (US); Amy Emerman, Ispwich, MA (US); Kruti Patel, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 441 days.

(21) Appl. No.: 16/721,395

(22) Filed: Dec. 19, 2019

(65) Prior Publication Data

US 2020/0199577 A1 Jun. 25, 2020

Related U.S. Application Data

(60) Provisional application No. 62/781,762, filed on Dec. 19, 2018.

(51) Int. Cl.
| | | |
|---|---|---|
| *C12N 15/10* | (2006.01) | |
| *C40B 50/16* | (2006.01) | |
| *C40B 50/18* | (2006.01) | |
| *C40B 70/00* | (2006.01) | |

(52) U.S. Cl.
CPC ..... *C12N 15/1058* (2013.01); *C12N 15/1065* (2013.01); *C12N 15/1093* (2013.01); *C40B 50/16* (2013.01); *C40B 50/18* (2013.01); *C40B 70/00* (2013.01); *C12Y 302/02027* (2013.01)

(58) Field of Classification Search
None
See application file for complete search history.

(56) References Cited

U.S. PATENT DOCUMENTS

| 8,288,097 B2 | 10/2012 | Mikawa | |
|---|---|---|---|
| 2012/0244525 A1 | 9/2012 | Hendrickson | |
| 2013/0303461 A1* | 11/2013 | Iafrate et al. | ........ C12Q 1/6806 514/183 |

FOREIGN PATENT DOCUMENTS

| WO | 2017129647 A1 | 8/2017 |
|---|---|---|
| WO | 2018136397 A1 | 7/2018 |

OTHER PUBLICATIONS

Kozarewa et al., "Overview of Target Enrichment Strategies," Curr. Protoc. Mol. Biol. 2015, 7.21.1-7.21.23. (Year: 2015).*
Margulies, et al., Nature 2005 437: 376-80.
Ronaghi, et al., Analytical Biochemistry 1996 242: 84-89.
Shendure, Science 2005 309: 1728.
Imelfort, et al., Briefings in Bioinformatics, 2009 10:609-618.
Fox, et al., Methods Mol Biol. 2009; 553:79-108.
Appleby, et al., Methods Mol Biol. 2009;513:19-39.
English, PLoS One. 2012 7: e47768.
Morozova, Genomics, 2008 92:255-64.

* cited by examiner

*Primary Examiner* — Kaijiang Zhang
(74) *Attorney, Agent, or Firm* — New England Biolabs, Inc

(57) ABSTRACT

The present disclosure provides, among other things, a way to amplify and sequence target sequences in a low-input sample. In some embodiments, the method comprises ligating a double-stranded adaptor onto a population of fragments to produce tagged fragments, and linearly amplifying the tagged fragments.

24 Claims, 6 Drawing Sheets

Specification includes a Sequence Listing.

TARGET ENRICHMENT

CROSS-REFERENCE

This application claims priority to U.S. Provisional Application No. 62/781,762 filed Dec. 19, 2018, which is hereby incorporate in its entirety by reference.

BACKGROUND

Next-generation sequencing (NGS) has become a major tool in genomics research, providing a powerful way to study DNA samples. There is an intense effort to develop NGS-based methods for the analysis of genomic variation. As part of this effort, several methods have been developed that enrich for specific target sequences, e.g., sub-regions of a genome. For example, target enrichment can be useful when only a portion of a genome needs to be analysed. For example, target enrichment can be used to enrich for the 'exome' (i.e., all transcribed sequences), or smaller sets of genes or genomic regions that are implicated in a particular disease or pathway. For example, target enrichment may be used to select the DNA for a set of cancer genes prior to sequence analysis. Selectively recovering target sequences should, in theory, reduce cost and increase sequencing depth relative to whole-genome sequencing.

It can be challenging to perform target enrichment on low input samples, largely because there is only a limited amount of DNA in the sample but also because the enrichment methods themselves are inefficient. Thus, there is therefore still a need for new methods for target enrichment, particularly methods that can be used for low input samples such as cfDNA and DNA that has been isolated from tissue sections.

SUMMARY

Provided herein are methods for enriching for target sequences in a preparation of polynucleotides. In some embodiments, this method may comprise: ligating a double-stranded DNA adaptor to each end of double-stranded polynucleotide fragments in a population of double-stranded polynucleotide fragments from a sample, wherein the DNA adaptor comprises: a 3' bottom strand and a 5' top strand wherein (i) the 3' bottom strand comprising, from 3' to 5': a primer binding sequence of at least 8 nucleotides, a sequence that that is complementary to the top strand and optionally a sample tag and/or a unique molecule identifier (UMI), and; (ii) the 5' top strand that does not contain a sample tag, an UMI or a primer binding sequence, and wherein at least some of the population of polynucleotide fragments contain a target sequence; (b) adding a polymerase and a primer to the adaptor ligated double-stranded polynucleotide fragments; (c) separating the top and bottom strands; and (d) generating a plurality of top strand complementary sequences from the top strand and a plurality of bottom strand complementary sequences from the bottom strand of the polynucleotide fragments by linear amplification.

In a further embodiment, the method further comprises removing the top strand of the ligated adaptor by cleaving the 5' top strand with a glycosylase wherein the top strand of the adaptor comprises one or more modified nucleotides where examples of the one or more modified nucleotide and glycosylase include deoxyuridine and uracil-DNA glycosylase (UDG).

In a further embodiment, the method as described in (d) further includes hybridizing a sequence-specific oligonucleotide attached to an affinity binding domain, to the complementary sequences of the top strands and/or the bottom strands of the target sequences in the polynucleotide fragments to form complexes.

The sequence specific oligonucleotide may have the same or different complementary sequences to the complementary sequence of the top and bottom strands of the target sequence in the polynucleotide fragments.

In some embodiments, the above described method further includes an additional step (e) binding the complexes to a solid support. Examples of an affinity binding domain and solid support used in these embodiments are biotin and streptavidin. Other affinity binding domains and supports known in the art may be alternatively used. One form of a support is beads but other supports such as columns etc. may be used. Preferably the oligonucleotides are in solution for the hybridizing step. However, oligonucleotide may be immobilized prior to binding to the target sequence.

In one embodiment, the above described method further includes hybridizing the oligonucleotide to a sequence at the 3' end of the target sequence in the polynucleotide fragment.

In one embodiment, the above described method further includes removing any overhanging polynucleotide sequence at the 3' end of the oligonucleotide hybridized complementary strand using a 3'-5' single strand exonuclease or a plurality of 3'-5' exonucleases for forming a blunt end duplex of the 3' end of the complement and the 5' end of the oligonucleotide. More particularly, this removal step can occur after linear amplification and before hybridization in (d) above or it can occur after hybridizing in (d) and before binding in (e) or it can occur after (e) when the complexes have been bound to a solid support. In one embodiment of the method, the overhanging polynucleotide sequence is not removed before adding a second adaptor or primer.

In one embodiment, the methods described above may include incorporating an index sequence in a second adaptor or a primer, for adding to the 3' end of the target sequence.

In some embodiments, the methods described above may further comprise amplifying the complement to the top strand and/or the complement to the bottom strand for sequencing of one or both of the strands.

In some embodiments, the methods described above may further comprise: combining a plurality of populations of polynucleotide fragments, where the adaptor contains the sample tag according to (a) and the fragments are linearly amplified according to (d).

In some embodiments, the methods described above may further comprise: sequencing the plurality of the populations of polynucleotide fragments.

In some embodiments, a method is provided for enriching for target sequences in multiple biological samples each characterized by a genome that comprises: (a) obtaining duplex polynucleotide fragments from the genomes of multiple samples; (b) ligating first adaptors to the fragments from each sample wherein each sample is in a separate reaction mix and wherein the first adaptors comprise a 5' top strand comprising from 5' to 3', a leader sequence, a sample tag, and a sequence that is complementary to a 3' bottom strand, where the 3' bottom strand contains at least one modified nucleotide and not the sample tag nor the leader sequence and wherein at least some of the polynucleotide fragments in each sample contain a target sequence; (c) pooling the ligated polynucleotide fragments into a single reaction mix where each sample contains a different sample tag,; (d) hybridizing an oligonucleotide having an affinity binding domain to the 3' end of the target sequence on each strand of the pooled polynucleotide fragments and immobilizing the hybridized oligonucleotide on a substrate;

(e) removing any 3' non-target single stranded overhang sequences to form a double-stranded end of the polynucleotide fragment; (f) ligating a second adaptor, optionally having an index sequence, to the 3' double-stranded end of the polynucleotide fragment, wherein (i) the 3' adaptor has a duplex at its 5' end and a 3' single strand overhang with a terminal 3'-5' exonuclease blocking moiety on its 3' end, and (ii) the duplex 5' end has a 5' top strand and a 3' bottom strand where the 3' bottom strand has at least one modified nucleotides; (g) removing the bottom strand of the second adaptor by enzymatic degradation at the modified nucleotides to form a single stranded DNA immobilized on a substrate by the hybridized oligonucleotide; (h) removing immobilized polynucleotides that do not contain target sequences using a 3'-5' double-stranded exonuclease; and (i) obtaining the enriched target sequences.

In a further embodiment, the methods described above may further comprise, introducing the index tag in the first adaptor, the second adaptor or during library amplification.

In a further embodiment, the methods described above may further comprise in step (e) using a 3'-5' single stranded exonuclease or a plurality of 3'-5' exonucleases to remove the 3' non target single stranded region.

In a further embodiment, the 5' top strand of the first adaptor used in the methods described above in (b) may further comprise a sample tag and/or a UMI.

In a further embodiment, the modified nucleotides of the first adaptor or the second adaptor used in the methods described above may further comprise deoxyuridine and enzyme degradation may be achieved using UDG.

In a further embodiment, the methods described above may further comprise amplifying the immobilized polynucleotides in (g) using a primer optionally containing an index sequence. An index sequence is not absolutely required. If it is added to the target sequence, it may be added in the first adaptor (bottom strand) or second adaptor (top strand) or in a primer used for library amplification.

In a further embodiment, the methods described above may further comprise pooling the polynucleotides with a single index sequence with other polynucleotides having different index sequences.

In a further embodiment, the methods described above may further comprise in step (i) sequencing the pooled DNA in a single sequencing reaction to determine the genotype of multiple biological samples.

In some embodiments, a method is provided for reducing contamination of a target sequence library by off-target polynucleotides, comprising: (a) obtaining a mixture of immobilized polynucleotides on a substrate wherein the polynucleotides comprise a duplex region and a single stranded region and wherein the mixture comprise: (i) non-specifically adsorbed polynucleotides corresponding to off target polynucleotides bound to a solid support (ii) specifically adsorbed polynucleotide complexes wherein the complex comprises a target DNA strand ligated to 3' and 5' adaptor sequences, wherein the target strand is hybridized to a target-specific polynucleotide attached to an affinity binding domain bound to the solid support; (b) subjecting the mixture to a double-stranded 3'-5' exonuclease so that the non-specifically adsorbed polynucleotides are degraded while the specifically adsorbed polynucleotide duplexes are not degraded; and (c) obtaining a target sequence library from the specifically adsorbed polynucleotide complexes.

In a further embodiment, in the methods described above, the specifically adsorbed polynucleotides are protected at their 3' end from 3'-5' double-stranded exonuclease activity by a 3' terminal blocking moiety.

BRIEF DESCRIPTION OF THE FIGURES

The skilled artisan will understand that the drawings, described below, are for illustration purposes only.

The drawings are not intended to limit the scope of the present teachings in any way.

FIG. 6A shows passing filter (PF) reads.

FIG. 6B shows alignment of the PF reads to the genome.

FIG. 6C shows the percentage of inserts that map to the target sequences of interest.

FIG. 6D shows that after removal of all duplicate sequences, the mean target coverage depth is at least 50 for each of 96 samples.

FIG. 6E shows the median insert size of the enriched sequences.

DETAILED DESCRIPTION

Figure 1:
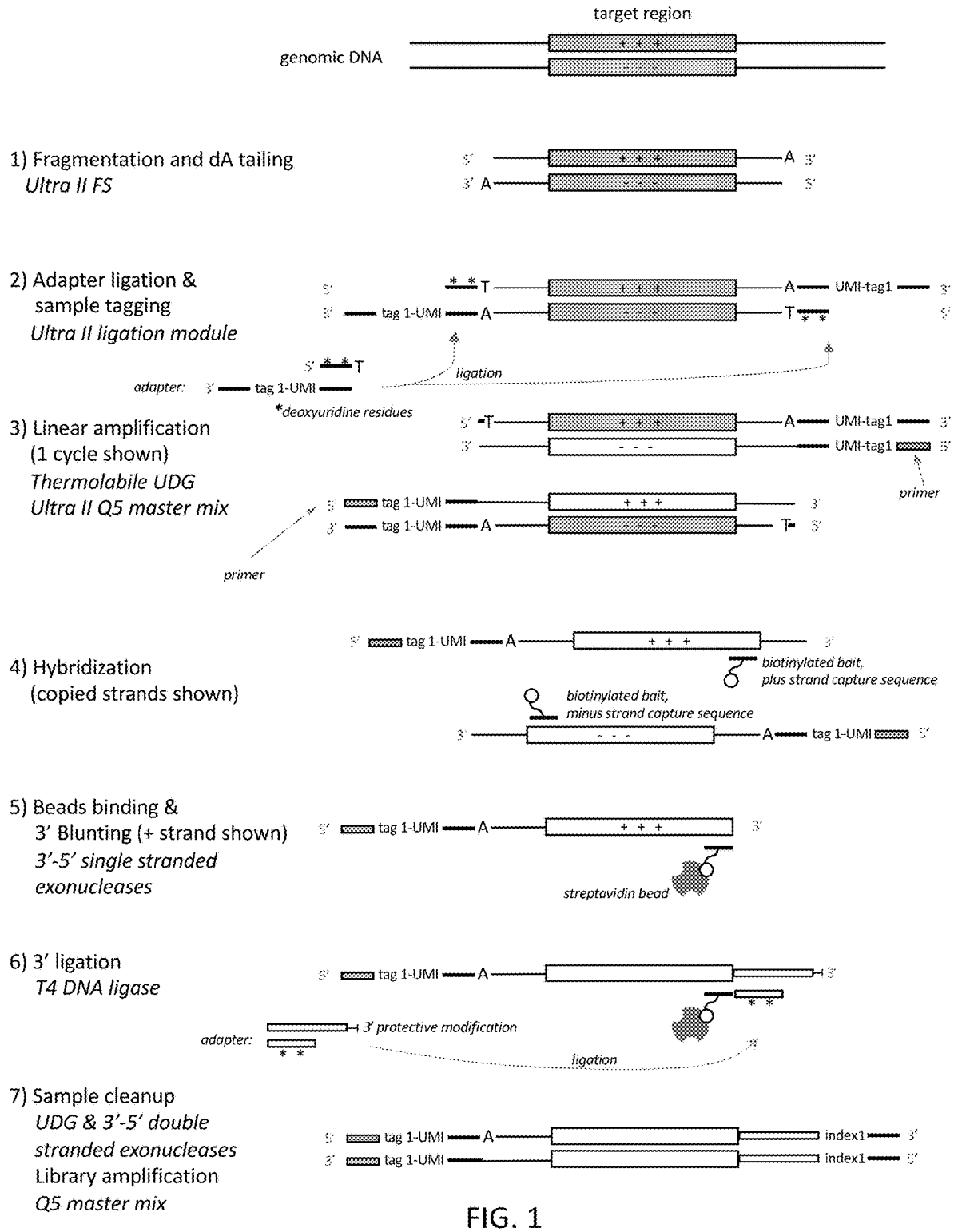
FIG. 1 shows one exemplary way in which the present amplification method may be implemented.

Before the various embodiments are described, it is to be understood that the teachings of this disclosure are not limited to the particular embodiments described, and as such can, of course, vary. It is also to be understood that the description of particular embodiments is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this invention belongs. Still, certain elements may be defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Numeric ranges are inclusive of the numbers defining the range. Unless otherwise indicated, nucleic acids are written left to right in 5' to 3' orientation; amino acid sequences are written left to right in amino to carboxy orientation, respectively.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

As used herein, the term "linear amplification" is intended to refer to an amplification reaction in which the amount of product increases linearly, not exponentially, over time.

The term "strand" as used herein refers to a nucleic acid made up of nucleotides covalently linked together by covalent bonds.

In its double-stranded form, DNA has two complementary strands of nucleic acid referred to herein as the "top" and "bottom" strands, where the top strand is, by convention, the strand that is oriented in the 5' to 3' direction.

If a double-stranded adaptor contains a top strand and a bottom strand, the different strands can be formed from different oligonucleotide molecules (as exemplified in FIG. 1) or can be formed by folding of a single molecule. In the latter case, the double-stranded adaptor may be in the form of a hairpin composed of a single oligonucleotide that has ends that base pair with one another to form a loop adaptor (see, e.g., U.S. Pat. No. 8,288,097 and US 2012/0244525A1). In some embodiments, after ligation, a region of a hairpin or loop adaptor can be cleaved to produce a duplex in which the top and bottom strands are on different molecules. In some cases, the cleaved region of a hairpin adaptor may contain a modified residue such as deoxyuridine, and the base can be cleaved using a glycosylase (e.g., UDG), although other methods are known.

The term "unique molecule identifier" (UMI) refers to a random unique sequence of at least 6 nucleotides (6N). Longer random unique sequences may be used, for example, 2-15 nucleotides, 6-12 nucleotides, or 8-12 nucleotides. The adaptors at each 3' end of a single molecule in steps 1 and 2 of FIG. 1 may have a different UMI. Hence, the UMI becomes a unique identifier for one strand of a single duplex The term "sample identifier" and "sample tag" are used interchangeable and refer to a molecular barcode that identifies the sample source of a population of polynucleotide fragments. Accordingly, the adaptors ligated at to each strand in a duplex will have the same sample identifier as will other polynucleotide fragments in the population (Tag-1 in FIG. 1).

Figure 2:
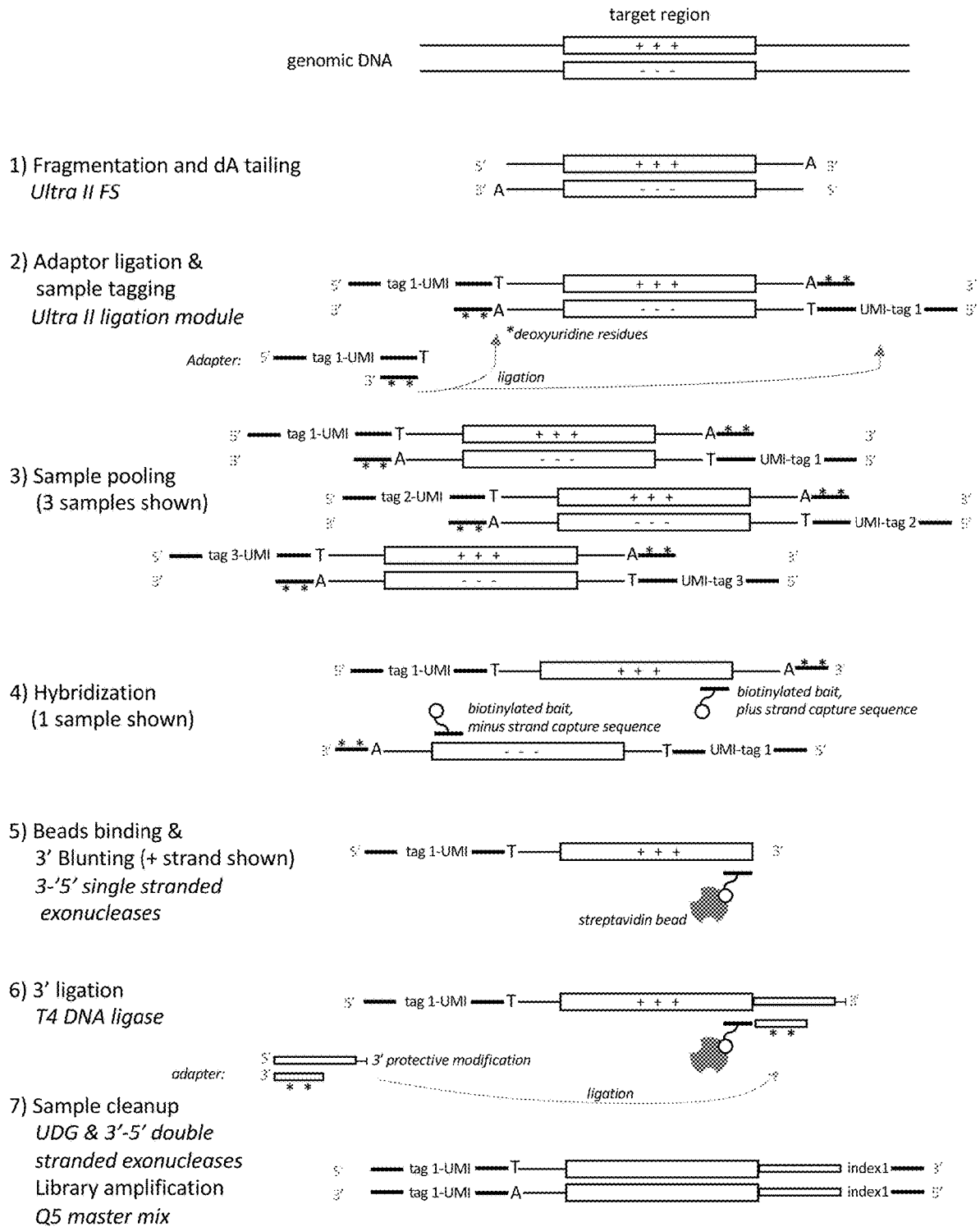
FIG. 2 shows one exemplary way in which the present method may be multiplexed.

The terms "index" and "index sequence" are used interchangeably. A single index sequence is used to label a multiplexed mixture of polynucleotides from a plurality of samples. The term " high sensitivity" for sequencing reads refers to the detection of rare variants that may occur in genomes. For example, in cancer biopsies, only a small percentage e.g. 0.1% of a population of polynucleotides from a human sample may contain the sequence variant of interest (e.g. SNPs). Therefore, a method that has a high sensitivity is necessary to detect these rare events. The methods involving linear amplification described herein and exemplified in FIG. 1 are high sensitivity methods. The term "low sensitivity" is used to refer to genotyping that requires a binary answer for example, whether a target variation is homozygous or heterozygous. The multiplexing methods described herein and exemplified in FIG. 2 provide a method that does not involve intermediate amplification steps before library amplification.

The term "sample" is used herein to refer to the source of a population of polynucleotide fragments. Depending on its context, a sample may be a single cell, a tissue or an individual biological entity such as a plant, animal or microbe.

The term "population of polynucleotides" refers to more than one polynucleotide. A population of polynucleotides may be derived from part or all of: a genomic DNA, organelle DNA, cDNA, or mRNA library.

The term "polynucleotide" refers to a DNA or an RNA. This molecule may be naturally occurring and derived from a genome (DNA) of a virus or other life form, or cytoplasm or nucleus (RNA) or may be synthetic. Polynucleotides may include an entire genome, gene, fragment of DNA or library of fragments. Polynucleotides may include ribosomal RNA (rRNAs), messenger RNAs (mRNAs), silencing RNAs (siRNAs), small nuclear RNAs (snRNA) microRNAs (miRNA) short interfering RNAs, (siRNAs) or long non-coding RNAs (lncRNAs).

The term "polynucleotide fragments" refers to products of polynucleotide cleavage or fragmentation.

The term "target sequence" refers to a piece of the polynucleotide fragment that contains a locus of interest. This may be because the target sequence contains sequences or mutations that when determined by sequencing can be diagnostic for e.g. disease, phenotype or genotype. Examples of target sequences include exons, introns, regulatory sequences, single nucleotide polymorphisms (SNPs), gene fusions, copy number variations, and indels. Analysis of target sequences may also be used to determine heterozygosity and homozygosity.

The present disclosure relates generally to compositions, methods of use, kits for obtaining sequencing data from polynucleotide samples and detecting variants that may be correlated with disease or with heredity. Examples are proved herein for linear amplification of polynucleotide samples providing the opportunity to distinguish sequences for positive and negative strands of a duplex DNA sample.

Examples are also provided for multiplex analysis of polynucleotide samples. Target enrichment methods may comprise linear amplification without multiplexing, multiplexing without linear amplification, or linear amplification and multiplexing, in each case, prior to hybridization and affinity capture. Linear amplification may provide or improve accuracy and coverage when processing low abundance samples.

Methods disclosed here may produce products that when sequenced, result in as much as 90% or more of reads on target, have very high coverage uniformity, and/or display minimal GC bias. Target-specific probes may be selected to capture a single gene or many targets in a multiplex workflow.

Certain principles of embodiments of the present method are shown in FIG. 1 and FIG. 2.

Sample Preparation

The first step of the method as described in FIG. 1 involves producing a population of A-tailed fragments. The purpose of A-tailing is to facilitate ligation of adaptors which can be efficiently achieved using kits provided by New England Biolabs, Ipswich, Mass. (e.g. NEBNext® Ultra™ II FS). Alternatively, other means for ligating adaptors to double-stranded DNA in a particular orientation may be used, or similarly A-tailing may be achieved by using kits from other vendors.

The sample used in present embodiments can contain genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein in certain embodiments, the mammal is a human.

In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene).

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human.

In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood from the blood of a subject (e.g., a cancer patient). The DNA fragments used in the initial step of the method should be non-amplified DNA that has not been denatured beforehand.

The DNA in the initial sample may be made by extracting genomic DNA from a biological sample, and then fragmenting it. The fragmenting may be done mechanically (e.g., by sonication, nebulization, or shearing) or enzymatically using a double-stranded DNA "dsDNA" Fragmentase® enzyme (New England Biolabs, Ipswich Mass.) or other single-stranded or double-stranded nucleases or nickases. In other embodiments, the DNA in the initial sample may already be fragmented (e.g., as is the case for FFPE samples and circulating cell-free DNA (cfDNA), e.g., ctDNA). The fragments in the initial sample may have a median size that is below 1 kb (e.g., in the range of 50 bp to 500 bp, or 80 bp to 400 bp), although fragments having a median size outside of this range may be used. In this method the ends of fragmented DNA may be polished and A-tailed prior to ligation to the adaptor.

In some embodiments, the amount of DNA in a sample may be limiting. For example, the initial sample of fragmented DNA may contain less than 200 ng of fragmented human DNA, e.g., 10 pg to 200 ng, 100 pg to 200 ng, 1 ng to 200 ng or 5 ng to 50 ng, or less than 10,000 haploid genome equivalents (e.g., less than 5,000, less than 1,000, less than 500, less than 100 or less than 10), depending on the genome, although amounts outside of these ranges may be used.

In some embodiments, the nucleic acid sequences may be fragmented to a desired size for example, an average size of 150 bp-200 bp or 200 bp-300 bp or 300 bp-400 bp or 400 bp-500 bp or 500 bp-600 bp or 600 bp-700 bp, although sizes outside of these ranges may be used. As illustrated as step 1 in FIG. 1, DNA fragmentation and A-tailing may be performed enzymatically using NEBNext Ultra II FS DNA Library Prep Kit reagents, for example. Following this step, a DNA polymerase adds a single deoxyadenosine residue to the 3' end of each sample DNA strand. This enables efficient ligation of adaptor sequences to the A-tailed fragments in the next step. Fragments having blunt or other types of overhanging ends can also be used in this method.

Adaptor Ligation

Next, the method may comprise ligating a double-stranded adaptor onto the population of fragments to produce tagged fragments. The double-stranded 5' adaptor can be composed of two oligonucleotides that are hybridized together (as exemplified in FIG. 1) a hairpin or loop adaptor. In some embodiments the fragments may be tailed with a 3' A (i.e., "A-tailed") and the adaptor may have 5' overhang of a T or U. These adaptors have a double-stranded region and, as such, can be considered double-stranded adaptors. As illustrated in FIG. 1 (step 2) the adaptor ligated in this step of the method is a double-stranded molecule, wherein one strand (the top strand) ligates to the 5' end of the nucleic acid sequence fragments, and the other strand (the bottom strand) ligates to the 3' end of the nucleic acid sequence fragments. As shown, the top strand of the adaptor base pairs with the bottom strand of the adaptor. In some embodiments (and as shown in FIG. 1), the top strand of the adaptor may comprise one or more (e.g., one, two or three) modified nucleotides, e.g., deoxyuridines, 8-oxoguanines or deoxyinosine that can be removed enzymatically, e.g., using a glycosylase. The top strand of the adaptor should be at least 10 nucleotides, e.g., at least 15 nucleotides, in length, although shorter top strands may be used in certain cases. Either way, the modified nucleotides enable the top strand to be completely removed before linear amplification is performed. The bottom strand of the adaptor may contain: i. a primer binding sequence, preferably only at the 3' end of the adaptor, of at least 8 (e.g., at least 10 or at least 15) nucleotides (e.g., the complement of an NGS platform-specific sequencing primer site), ii. optionally a molecular barcode (sample tag) and optionally an UMI, and iii. a sequence that is complementary to the top strand. The UMI, if it is present in the adaptor, can be a random unique sequence of at least 6 nucleotides (i.e., composed of 6Ns), but longer random unique sequences may be used in many cases. In some embodiments, a less complex UMI may be used. In some embodiments, the adaptor does not contain a UMI. As shown, in some embodiments, the adaptor comprises single nucleotide 5' overhang at the end of the adaptor that ligates to the fragments. In these embodiments, the single nucleotide overhang may base-pair with the 3' A-tail of the fragments and, as such, may be a T or a U. In other embodiments, a blunt-ended adaptor or an adaptor that has another type of overhang may be used. The adaptor sequence and molecular barcode are single-stranded in the adaptor shown in FIG. 1. Ligases that may be used in adaptor ligation include T4 DNA ligase, circligase and TaqDNA ligase, although other ligases may be substituted.

After ligation, if necessary, the nucleic acid fragments ligated to adaptors can be purified from the ligation reaction mixture, e.g., using magnetic beads.

Linear Amplification

In some embodiments of the method (in accordance with step 3 of the method shown in FIG. 1) the tagged fragments may be linearly amplified by thermocycling the tagged fragments in the presence of a thermostable polymerase and a single primer that hybridizes to the primer binding sequence of the bottom strand of the adaptor. As shown, this step produces 5' tagged linear amplification products.

In embodiments in which the top strand of the double-stranded adaptor comprises one or more modified nucleotides, prior to the linear amplification, the tagged fragments may be treated with an enzyme, e.g., a glycosylase to remove sugars from the modified nucleotides prior to thermocycling resulting in cleavage and removal of the DNA containing these modified nucleotides.

In these embodiments, the modified nucleotide may be deoxyuridine and the enzyme may be UDG, although other modified nucleotide/enzyme combinations can be used. In the example shown in FIG. 1, a deoxyuridine-containing adaptor sequence ligated to the 5' end of the nucleic acid fragments is treated with UDG. In some embodiments, Antarctic Thermolabile UDG (New England Biolabs, Ipswich, Mass.) may be used for this step because that enzyme is thermolabile. UDG catalyzes the release of free uracil from the adaptor sequences ligated to the 5' end of the DNA fragments and produces abasic sites in the adaptor sequence. Abasic sites are susceptible to hydrolytic cleavage and break apart at the elevated reaction temperatures in the following thermocycling reaction.

The linear amplification may be done by combining the linear polynucleotide fragment ligation products with polymerase, dNTPs, a linear amplification primer and optionally UDG to produce a reaction mix, and thermocycling the reaction mix. The reaction mix should be thermocycled at least at least once (e.g., at least 5 times, or at least 10 times or at least 20 times) to produce a number of copies of each DNA fragment that are ligated to the bottom strand of the adaptor and where the copy number corresponds to the cycle number. The products of this reaction have a copy of the molecular barcode of the bottom strand of the adaptor at the 5' end and therefore can be referred to as 5'-tagged amplification products. This reaction can be done using NEBNext Ultra II Q5® Master Mix (A master mix containing Q5 DNA polymerase (New England Biolabs, Ipswich, Mass.)), although other polymerases can be used.

This linear amplification step can be implemented as follows. After an initial denaturation step (e.g., at 98° C. for 30 seconds), the reaction can be temperature cycled at least once (e.g., at least 5 times, at least 10 times, at least 15 times or at least 20 times) in the following way: a temperature above 90° C. (e.g., 98° C.) for at least 5 seconds, a temperature of below 60° C. (e.g., 55° C.) for at least 5 seconds, and a temperature in the range of 65° C. to 80° C., e.g., 70° C. to 75° C. for at least 10 seconds. At the first temperature, e.g., 98° C., the DNA fragments denature. At the next temperature, e.g., 55° C., the linear amplification primer anneals to the 3' end of the adaptor sequence. At 72° C., the polymerase (e.g., Q5 polymerase) extends the linear amplification primer. Other thermocycling conditions are known and can be readily used in this step. The product is a DNA sequence fragment containing an adaptor sequence at the 5' end, i.e., a 5' tagged amplification product.

In some embodiments, the mixture is incubated at 37° C. for 10 minutes (which is suitable for Antarctic thermolabile UDG) and then thermocycled.

In one example, after the UDG treatment the reaction can be heated and cooled any number of times, e.g., once, twice, at least 5 times, at least 10 times or up to 20 times to produce up to 20 5'-tagged amplification product molecules, where each molecule is a copy of a single DNA fragment that is ligated to a bottom strand of the adaptor.

In some embodiments, the polymerase used in this step of the method should have a low error rate. In some embodiments, the polymerase may be a proofreading DNA polymerase, which typically have a 3' to 5' exonuclease activities. Examples of non-proofreading thermostable polymerases (i.e., thermostable polymerases that do not have a 3' to 5' exonuclease activity) include, but are not limited to, Taq and Tth. Examples of proofreading thermostable polymerases include, but are not limited to, Pfu (Agilent Technologies, Santa Clara, Calif.), Pwo (Roche, Basel, Switzerland), Tgo (Roche, Basel Switzerland), VENT® (New England Biolabs, Ipswich, Mass.), DEEP VENT® (New England Biolabs, Ipswich, Mass.), KOD HiFi (Novagen, Madison, Wis.), PFX50™ (Invitrogen, Waltham, Mass.), HERCULASE II™ (Agilent Technologies, Santa Clara, Calif.), PLATINUM PFX™ (Life Technologies, Waltham, Mass.) and ProofStart™ (Qiagen, Hilden, Germany). These polymerases, on average, produce 4× to 8× fewer errors than Taq polymerase. Further examples of proofreading thermostable polymerases include, but are not limited to, PHUSION® (Thermo Fisher Scientific, Waltham, Mass.), PFUULTRA™ (Agilent Technologies, Santa Clara, CA), PFUULTRA™ II (Agilent Technologies, Santa Clara, Calif.), IPROOF™ (Bio-Rad, Hercules, Calif.), Q5 polymerase, and KAPAHIFI™ (Kapa Biosystems, Wilmington, Mass.). These polymerases, on average, produce at least 20× fewer errors than Taq polymerase and can be readily employed herein. In some embodiments, it is envisaged that isothermal amplification methods might be used instead of thermocycling where such methods were capable of utilizing a single primer binding site. Examples of amplification methods include ligase chain reaction (LCR), strand displacement amplification (SDA), transcription mediated amplification (TMA), self-sustained sequence replication (3SR), Qβ replicase based amplification or rolling circle amplification, nucleic acid sequence-based amplification (NASBA), repair chain reaction (RCR), boomerang DNA amplification (BDA) helicase dependent amplification (HDA).

Hybridization

In some embodiments of the method (in accordance with step 4 of the method shown in FIG. 1), the 5' tagged amplification products may be hybridized to target-specific oligonucleotides to produce complexes. In the embodiment shown, the target-specific oligonucleotides (referred to as "baits") may be biotinylated. The target-specific oligonucleotides may be designed to hybridize to any targets, e.g., target sequences in cancer-related genes, etc. This step of the method may use at least 1, at least 5, at least 10, at least 100, at least 1,000 or at least 10,000 target-specific oligonucleotides so that different regions of the genome can be captured and enriched. The oligonucleotides themselves may be in the range of 30-100 nucleotides in length, but lengths outside of this range may be used in some cases. As shown, some oligonucleotides may come in pairs, where one target-specific oligonucleotide hybridizes to a target sequence in the top strand of a region of interest, and the other target-specific oligonucleotide hybridizes to a target sequence in the bottom strand of a region of interest. A target sequence may lie at the 3' end of a region of interest. In some embodiments, biotinylated target-specific oligonucleotides are added to a hybridization solution containing the pool of DNA fragments. The hybridization solution containing the target-specific oligonucleotides and DNA fragments is then incubated to allow the target-specific oligonucleotides to hybridize 5' tagged amplification products that comprise a target sequence. This hybridization may be done under relatively high stringency or relatively low stringency. If low stringency conditions are used, a significant amount of non-specific binding to the target-specific oligonucleotides may occur. Non-specifically bound sequences can be removed by treatment with a 3'-5' single-stranded or double-stranded exonuclease (e.g., exonuclease III) in a subsequent step.

In some embodiments the complexes can be bound to a solid support via a capture group (e.g., biotin) on the target-specific oligonucleotides. This step enriches for 5' tagged amplification products that comprise a target sequence. For example, if the target-specific oligonucleotide is biotinylated and the complexes can be enriched by binding to a support comprised of streptavidin beads. In some embodiments, magnetic beads coated in streptavidin can be added to the reaction mix after hybridization of the a 5' tagged amplification products to the target-specific oligonucleotides. The magnetic beads can be isolated by magnetism and then washed, thereby enriching for complexes that comprise the 5' tagged amplification products. An alternative to biotin includes a SNAP-tag® (New England Biolabs, Ipswich, Mass.) that is a protein that reacts with a benzylguanine and may be modified to bind to an affinity capture domain.

The solid support may include a matrix formed from the affinity capture domain or coated with the affinity capture domain. A solid support may be, for example, a bead including a magnetic bead, a column, a porous matrix, or a flat surface formed from for example, plastic or paper.

Production of Blunt Ends

In some embodiments of the method (in accordance with step 5 of the method shown in FIG. 1), after the beads have been washed, the complexes that are tethered to the beads may be treated with a single-stranded 3'-5' exonuclease to remove any overhanging 3' end from the 5' tagged amplification products and produce a flush end at the 3' end of the target sequence. One or more single stranded 3'-5' exonucleases may be used individually or in combination to catalyze stepwise removal of mononucleotides from 3' ends of single-stranded DNA. For example, exonuclease I and exonuclease T can be used individually or in combination. The 3'-5' single strand exonuclease will trim the 3' end of the captured 5'-tagged amplification products until they are flush with the target sequence. After 3' blunting, the 3' adaptor is ligated to the 3' end of the target DNA. In an example, a 3' nuclease reaction buffer containing one or more single-stranded 3' exonucleases, can be added to the beads (which still contain 5' tagged amplification products to them) to create a reaction mix. After the reaction mix has been incubated (e.g., for approximately 5 minutes at 37° C., and then 5 minutes at 25° C.), the magnetic beads can be separated from the mix by a magnetism and washed. The mix can then be discarded because the exonuclease-treated complexes are still tethered to the beads.

Ligation of a 3' Adaptor

In some embodiments of the method (as illustrated in step 6 of the method shown in FIG. 1), another double-stranded adaptor may ligated onto the exonuclease-treated complexes, thereby adding a 3' adaptor sequence onto the 3' end of the target sequence to produce a ligation product comprising a 5' and 3' tagged strand (i.e., a strand that is tagged on both ends) comprising the target sequence. In some embodiments, the top strand of the 3' adaptor may be 3'-5' double-stranded DNA exonuclease resistant (by, for example, containing one or more phosphorothioate at the 3' end or other blocking moiety, or being single-stranded at the 3' end (as shown in FIG. 1) or part of a hairpin structure, which becomes single-stranded after it has been partially digested). In an example, the beads may be washed in a buffer and then resuspended in a ligation buffer. In one embodiment, a 3' adaptor sequence and T4 DNA ligase can be added to the ligation mixture to blunt end ligate the 3' adaptor to the target sequence. A-tailing the 3' end of the target sequence for ligation with an adaptor having a complementary T overhang may be an alternative option. Alternatively, other ligation methods known in the art may be used. These may include joining the 3' adaptor sequence to the target sequence by ligation using for example, a circ ligase or Taq ligase. In this example, the adaptor is a double-stranded molecule, with the top strand ligating to the 3' end of the nucleic acid sequence fragments, and the bottom strand containing several deoxyuridine residues or other modified nucleotides, as described above. The plus strand adaptor sequence contains a 3' adaptor sequence (e.g., NGS platform-specific sequencing primer site and a library amplification primer site). After incubation, e.g., at 20° C. for 15 minutes, the magnetic beads are then isolated from the ligation mixture using magnetism and separated from the ligation mixture. Again, the mix can then be discarded since the ligation products, which comprise a complex comprising a 5' and 3' tagged strand comprising the target sequence, are still tethered to the beads.

Sample Clean-Up and Amplification

In some embodiments of the method (as illustrated in step 7 of the method shown in FIG. 1), the ligation products, which comprise a 5' and 3' tagged strand comprising the target sequence are cleaned up by treatment with a double-stranded 3'-5' exonuclease that catalyzes the stepwise removal of mononucleotides from 3' ends of duplex DNA, and also cleaves abasic sites. The double-stranded 3'-5" exonuclease can both eliminate any remaining double-stranded off-target DNA molecules, and also cleave the abasic sites created by UDG, thus eliminating the unnecessary 3' adaptor strand from the subsequent steps. In an example, the magnetic beads may be washed and resuspended in 3'-double-stranded exonuclease buffer. A double-stranded 3'-5' exonuclease, e.g., exonuclease III, is added and the exonuclease mixture may be incubated (e.g., 15 minutes at 37° C.) thereby removing any remaining non-target sequences with unprotected or accessible double-stranded 3' ends. UDG or another deglycosylase can also be added, too, in order to remove the bases from the modified nucleotides (e.g., the deoxyuridines) from the 3' adaptor minus strand and render the resulting abasic sites sensitive to cleavage by the double-stranded 3'-5' exonuclease. The magnetic beads are then isolated from the reaction mix using magnetism and washed. Again, the mix can then be discarded since the exonuclease-treated ligation products, which comprise a complex comprising a 5' and 3' tagged strand comprising the target sequence, are still tethered to the beads. As noted above, the tagged strands can be rendered 3'-5' exonuclease insensitive and therefore the tagged strands should not be degraded by this exonuclease treatment.

The 5' and 3' tagged strands can be amplified by PCR, e.g., using a first primer that hybridizes to the 3' adaptor sequence and a second primer that hybridizes to the complement of the primer in the linear amplification products, to produce PCR products. In an example, the magnetic beads can be washed with a buffer and resuspended in a PCR mixture containing water, a PCR master mix and amplification primers. The following PCR cycling conditions is used: 98° C. for 30 seconds followed by 18 cycles of 98° C. for 10 seconds, 62° C. for 15 seconds and 72° C. for 20 seconds. At the end of the 18 cycles, the PCR mixture incubated at 72° C. for 5 minutes. The PCR products obtained from the target sequences are then quantified and sequenced using conventional methods.

Sequencing

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al. (Nature 2005 437: 376-80); Ronaghi et al. (Analytical Biochemistry 1996 242: 84-9); Shendure (Science 2005 309: 1728); Imelfort et al. (Brief Bioinform. 2009 10:609-18); Fox et al.(Methods Mol Biol. 2009; 553:79-108); Appleby et al. (Methods Mol Biol. 2009; 513:19-39); English (PLoS One. 2012 7: e47768); and Morozova (Genomics. 2008 92:255-64), which are incorporated by reference for the general descriptions of the methods and the particular steps of the methods, including all starting products, reagents, and final products for each of the steps. The sequence reads may be analyzed computationally to identify sequence variations in the sample, such as point mutations, in-dels, deletions, insertions and rearrangements.

Multiplexing

Advantages of multiplexing include (a) the ability to analyse a large number of samples in one sequence reaction while maintaining a means to track the source of each polynucleotide and each sample from which it came (b) pooling samples can increase efficiency and reduce cost of the workflow used to enrich targets and sequence samples. Multiplexing as described herein can involve pooling two, tens, hundreds or thousands of samples. A linear amplification step can be omitted for genotyping samples, where low sensitivity of detection is sufficient. Multiplexing in the absence of linear amplification can be used in any application where a low sensitivity screen for variants is desirable such as marker genotyping for molecular breeding programs (e.g., plants, livestock, and fishery breeding programs), human sample identification, and mouse-tail genotyping.

In some embodiments, the adaptor ligated onto the fragments in the initial step of the method may have a sample identifier which in FIG. 2 is indicated by the term "tag". In these embodiments, the reaction may be multiplexed by combining samples from different sources into a pool. The pool is recognized by an index sequence referred to in FIG. 2 as an "index". In these embodiments, the method may comprise ligating a double-stranded adaptor to individual polynucleotide fragments from a single sample having the sample identifier and then pooling the polynucleotide fragments with sample identifiers from multiple samples. Linear amplification is not required in the multiplex protocol for genotyping shown in FIG. 2. However, it may be included in the workflow. If the sample is subjected to linear amplification, then the primer binding sequence, sample identifier, and UMI are ligated onto to the 3' ends of the sample DNA. The primer binding site is not required when linear amplification is not performed as shown in FIG. 2. Moreover, a UMI is optional. During linear amplification, primer extension produces 5' tagged amplification products. Because we can cycle this reaction multiple times and create many copies of the sample DNA, this strategy is particularly useful for high depth of coverage sequencing needs, such as analysis of cfDNA. Alternatively, if the sample is not subjected to linear amplification, then an adaptor sequence having a sample identifier, and optionally a UMI may be ligated onto the 5' end of the sample DNA, as shown in FIG. 2. This strategy is particularly suitable for low-depth of coverage sequencing needs of samples that are not limiting, such as genotyping. The embodiment shown in FIG. 2 does not include the linear amplification step of the method shown in FIG. 1. The sample preparation, fragmentation, and A-tailing steps are same as those as described above, except multiple samples may be processed. In these embodiments, the double-stranded adaptor may comprise a bottom strand and a top strand that comprises a sample identifier positioned on the single strand extension located between a first single stranded adaptor sequence and the duplex region that contains a sequence that is complementary to the bottom strand. This step of the method results in multiple adaptor-tagged polynucleotide fragments that are each tagged with a different sample identifier, where the sample identifiers identify the sample to which they are tagged. In the embodiment shown, the double-stranded adaptor may have a top strand containing: a) a first adaptor sequence (which is used for amplification later in the protocol), b) a sample identifier sequence (tag), and optionally, c) a unique molecular identifier (UMI). As shown in FIG. 2, the bottom strand of the adaptor may optionally contain multiple modified nucleotides (e.g., deoxyuridine residues), which can enable strand specific cleavage in later steps of the protocol.

As shown, after all the samples have been ligated to adaptors that have a sample identifier and optionally a UMI sequence, the samples may be pooled in a single vessel and may progress through the rest of the steps shown in FIG. 2 en masse. Specifically, after pooling, the method may comprise hybridizing the pool of adaptor-tagged samples with a target-specific oligonucleotide to produce complexes. The complexes may be bound to a solid support, thereby enriching for 5' tagged molecules that comprise a target sequence. If the target-specific oligonucleotides are biotinylated, then the enrichment can be done using a support that comprise streptavidin (e.g., magnetic streptavidin beads). Next, in some embodiments, the method may comprise treating the complexes with a 3'-5' single strand exonuclease as in the workflow exemplified in FIG. 1 to remove any overhanging 3' ends from the product molecules and produce a flush end at the 3' end of the target sequence. However, this step is optional and a second adaptor can be added by other means. As shown, a second double-stranded adaptor can be ligated onto the flush end of the exonuclease-treated complexes, thereby adding a 3' adaptor sequence onto the 3' end of the target sequence to produce a 5' and 3' tagged strand comprising the target sequence. Other ligation strategies can be used in this step. For example, the exonuclease-treated complexes can be A-tailed and a T-tailed adaptor could be used. In many embodiments, the top strand of the second double-stranded adaptor may be 3'-5' double-stranded DNA exonuclease resistant because of a 3' blocking moiety. In these embodiments, the method may comprise treating the ligation products with a 3'-5' double-stranded exonuclease. The 5' and 3' tagged strands can then be amplified by PCR using a first primer that hybridizes to the 3' adaptor sequence and a second primer that hybridizes to the complement of the first adaptor sequence, to produce amplification products. In this step, an index tag can be added to identify the pool of samples in the multiplex reaction.

Figure 5:
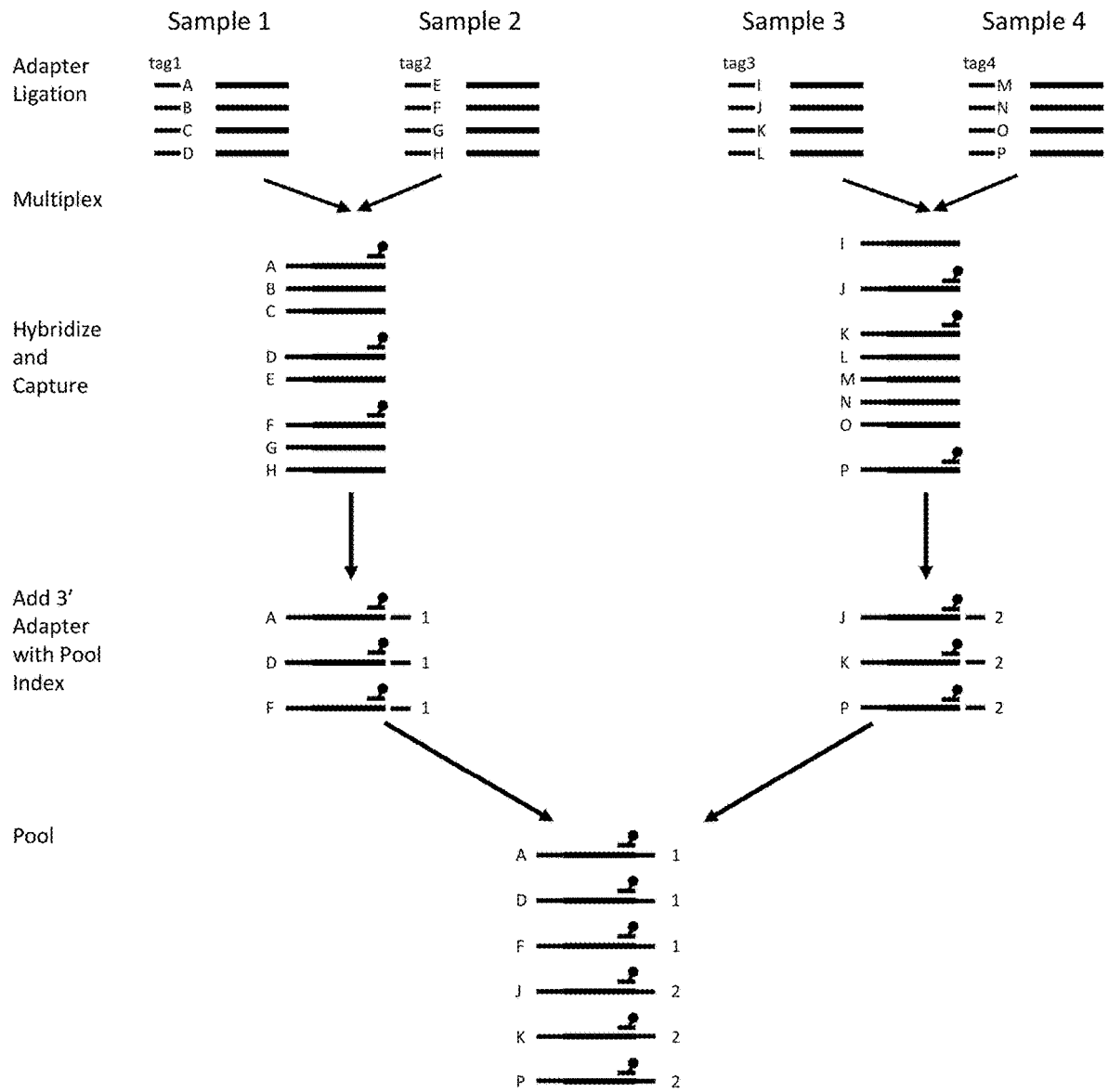
FIG. 5 shows a graphical representation identifying molecules, samples and batches in a multiplex reaction resulting in a single sequencing reaction. Four samples (1-4) with a different UMI but the same sample identifier is shown, each sample containing 4 polynucleotide fragments each with a different UMI. When sample 1 and 2 are pooled, and 3 and 4 are pooled, index tags are introduced by library amplification and all samples are pooled for a single sequencing reaction.
Figure 6A:
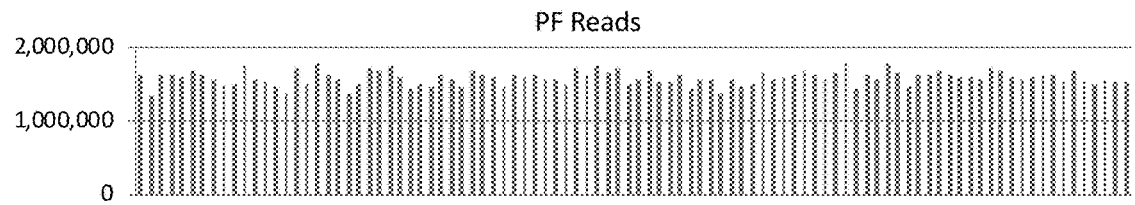
FIG. 6A-FIG. 6E show sequencing metrics that confirm that the data from pooling 96 samples is substantially equivalent for each sample.
Figure 6B:
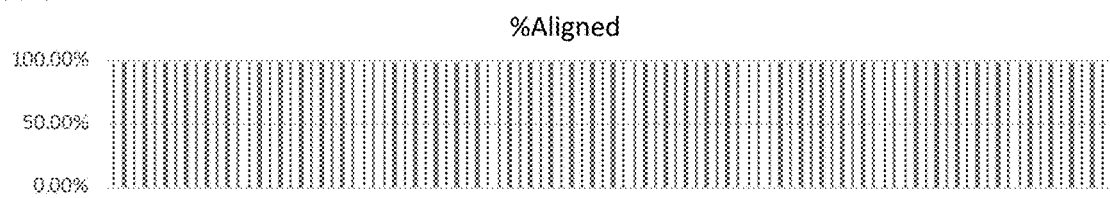
Figure 6C:
Figure 6D:
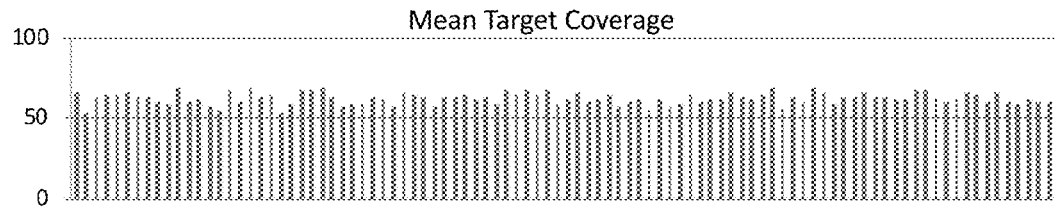
Figure 6E:
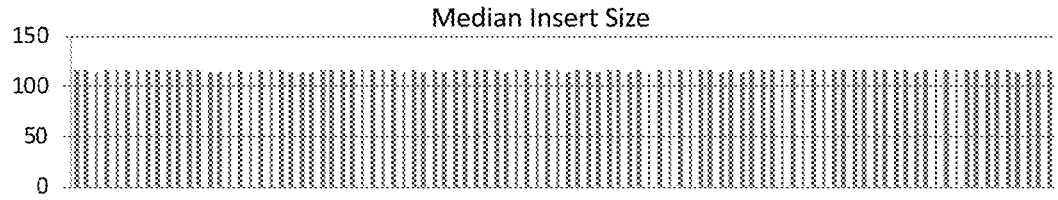

As described above, the amplification products may be sequenced by any convenient method to produce sequence reads that comprise the sequence, at least part of the target sequence and a sample identifier or complements thereof. During analysis, the sequence reads may be assigned to a sample on the basis of the sample identifier that is in the sequence read. This method may be implemented in a high-throughput way. As few as 1 and as many as 96 samples, or as many as 384 or more samples, each having different sample identifiers, may be pooled together where the pool is labeled with a single index on the 3' adaptor. These pooled samples each with a single index can then be pooled into larger pools containing multiple index sequences for analysis in a single sequencing reaction. A single sequencing reaction may include a multiplex enriched preparation of 3' adaptor and 5' adaptor ligated polynucleotide target sequences from one or more samples, 2 or more samples, 3 or more samples, 5 or more samples, 10 or more samples, 50 or more samples, 100 or more samples, 500 or more samples, 1000 or more samples, 5000 or more samples, up to and including about 10,000 or more samples where these samples may be obtained from the same or different sources. For example, the samples may be seeds of a plant, and the sources may be different plants. In this example, the original individual polynucleotide fragments containing a target sequence can be tracked by a UMI, each seed from which the polynucleotides came, can be tracked by a sample identifier and each plant for which the seeds came can be tracked by an index sequence. This is further illustrated in FIG. 5.

The foregoing example may include further multiplexing in connection with the hybridization. Hybridization reactions may be performed with single or pairs of target isolation probes or they may be multiplexed by performing each reaction with many hybridization probes (e.g., 3 or more, 5 or more, 10 or more, 100 or more, or 1,000 or more target isolation probes).

The ability to perform sequencing on multiplexes of multiplexed samples means that as many as several thousand or more samples can be analysed in a single sequencing run enabling a rapid and cost-effective analysis.

Kits

The present disclosure relates to kits for performing methods described herein. A kit, for example, may include any system for delivering materials or reagents for carrying out a method described herein. In some embodiments, kits can include systems that allow for the storage, transport, or delivery of reaction reagents (e.g., probes, enzymes, adaptors, primers, reaction reagents, reaction vessels and/or surfaces in appropriate containers) and/or supporting materials (e.g., written instructions for performing the assay, handling instructions) from one location to another. For example, in some embodiments kits include one or more enclosures (e.g., boxes) containing the relevant reaction reagents and/or supporting materials. Such contents may be delivered to the intended recipient together or separately. For example, a first container may contain an enzyme for use in an assay, while a second container may contain adaptors. A kit alone or in combination may be formulated for selecting and enriching target templates from a nucleic acid sample containing non-target and target sequences. A kit may include one or more adaptors as described herein, primers; exonucleases; ligase; polymerase(s); buffers; and nucleotides. A kit may further comprise one or more buffer solutions and standard solutions for the creation of a DNA library. These components may be present in a single reaction vessel or multiple tubes and may be packaged separately or together.

Automated Work Flows

Methods disclosed herein, may be performed with at least some automation. Systems for processing multiple samples in parallel may be adapted for use with the disclosed methods. For example, systems for processing samples in racks of tubes, multi-well plates, on droplets on surfaces, and/or through microfluidics (including variations that use pressure, electrical potential, acoustic forces, and/or other forces to manipulate fluids and contact materials). Methods disclosed herein may be performed, for example, using an Echo® 525 Liquid Handler (Labcyte, Inc., San Jose, Calif.) or by means of microfluidic devices or a lab on a chip (Aqua Drop, Sharp). For the methods shown in the FIG. 1 and Example 1, steps 1 and 2 are performed in a single buffer which then is replaced by a different buffer in step 3. Steps 4-7 can then be achieved in a single reaction tube by adding reagents sequentially or together. In example 2 and FIG. 2, again steps 1 and 2 are performed in a single reaction tube and then a change in buffer is required, sample pooling occurs and the remainder of the reaction (steps 4-7) can be performed in a single reaction vessel into which reagents are added sequentially or together. It is envisaged that the entire reaction from sample to sequence output may be capable of automation being performed in a single device.

It may be desirable in agricultural research, to analyze a particular single nucleotide polymorphism (SNP) profile from a single plant or multiple plants in a single sequencing reaction. Automated multiplexing may include assessing multiple target genomic regions of interest from multiple plants. This can be achieved in a platform that utilizes for example 96 well dishes where 5' adaptor ligation, hybridization, capture, enrichment and 3' adaptor addition is performed in individual wells of 96-well plates. Following 5' adaptor ligation of polynucleotide fragments from a single sample (part of a plant) is achieved, polynucleotide fragments from multiple samples (multiple plant parts) from all 96 wells can be combined into a single well in a second 96 well plate for capture enrichment and 3' adaptor ligation. Multiplexed samples from a plurality of wells in the second plate (multiple plants) may then be pooled for sequencing.

All patents and publications, including all sequences disclosed within such patents and publications, referred to herein including U.S. Provisional Application No. 62/781, 762 filed December 19, 2018, are expressly incorporated by reference.

EXAMPLES

Aspects of the present teachings can be further understood in light of the following examples of linear amplification without multiplexing (Example 1) and multiplexing without linear amplification (Example 2), which should not be construed as limiting the scope of the present teachings in any way.

Any reagents used herein that are not otherwise associated with a vendor, were obtained from New England Biolabs, Ipswich, Mass.

Example 1

An Enriched Library of Target Sequences from Human DNA Using Linear Amplification Human gDNA was added to NEBNext Ultra II FS reaction buffer and NEBNext Ultra II FS enzyme mix according to manufacturer's instructions (New England Biolabs, Ipswich, Mass.). NEBNext Ultra II FS enzyme mix contains enzymes that perform DNA fragmentation, end repair, and A-tailing. The mixture was cooled to 4° C., and a double-stranded adaptor (the first adaptor) was added, with the bottom strand being (SEQ ID NO: 1)
5′ GATCGGAAGAGCGTCGTGTAGGGAAAGAGTGTNNNNNNNNNNNN

AGGCTATAGTGTAGATCTCGGTGGTCGCCGTATCATT 3′.

A 12N (a random sequence of 12 nucleotides) UMI and a sample tag (the 8 bold underlined letters) were present in the adaptor. The top strand was complementary to nucleotides 1-32 of SEQ ID NO:1 (the portion on the 5′ side of the tag) and contained several deoxyuridine residues and a 3′ T overhang. NEBNext Ultra II Ligation Master Mix was added to the reaction mixture and incubated for 15 minutes at 20° C. (step 2 of FIG. 1). The DNA fragments were purified using New England Biolabs (Ipswich, Mass.) sample purification beads and eluted in nuclease free water.

DNA fragments in water were added to NEBNext Ultra II Q5 Master Mix, 2 μl Antarctic Thermolabile UDG, and linear amplification primer, with sequence 5′ AATGA-TACGGCGACCACC 3′ (SEQ ID NO:2). The reaction was incubated at 37° C. for 10 minutes, 98° C. for 30 seconds, and then subjected to 20 cycles of 98° C. for 10 seconds, 55° C. for 10 seconds, and 72° C. for 20 seconds, then a final incubation at 72° C. for 2 minutes (step 3 of FIG. 1).

This reaction was transferred to a hybridization mix (see NEBNext Ultra II Q5 PCR mix) that contained target isolation probes, each comprising a target-specific oligonucleotide (bait) and an affinity binding domain (namely, biotin), and incubated at 95° C. for 10 minutes, then 58° C. for 90 minutes (step 4 of FIG. 1). A target-specific oligonucleotide was designed to bind to the 3′ end of the target region. After hybridization, the target isolation probe/target DNA complexes were bound to hydrophilic streptavidin magnetic beads (New England Biolabs, Ipswich, MA) for 10 minutes at 48° C., then washed twice for 5 minutes at 62° C. with a wash buffer (step 5 of FIG. 1).

The beads were resuspended in a 3′-5′ single stranded exonuclease buffer with enzyme and incubated for 5 minutes at 37° C., and 5 minutes at 25° C. (step 5 of FIG. 1). The beads were then washed and resuspended in 1× Quick Ligation buffer (New England Biolabs, Ipswich, Mass.). Quick Ligase and a 3′ adaptor for ligation to the 3′ end of the target sequence was added to the buffer and incubated for 15 minutes at 20° C. (step 6 of FIG. 1). This 3′ adaptor had a protective modification on the 3′ end of the top strand and a bottom complementary strand with modified bases. The 3′ adaptor had a top strand sequence 5′ AGATCG-GAAGAGCACACGTCTGAACTCCAGTCAC 3′ (SEQ ID NO:4). The beads were then washed and resuspended in 100 μl of 1× NEBuffer 1 containing a 3′-5′double-stranded exonuclease and UDG and incubated for 15 minutes at 37° C. (step 7 of FIG. 1).

The magnetic beads were then washed and resuspended in a 1× NEBNext Q5 Hot Start HiFi PCR Master Mix containing NEBNext Direct® PCR primers (New England Biolabs, Ipswich, Mass.) for PCR amplification.

Figure 3:
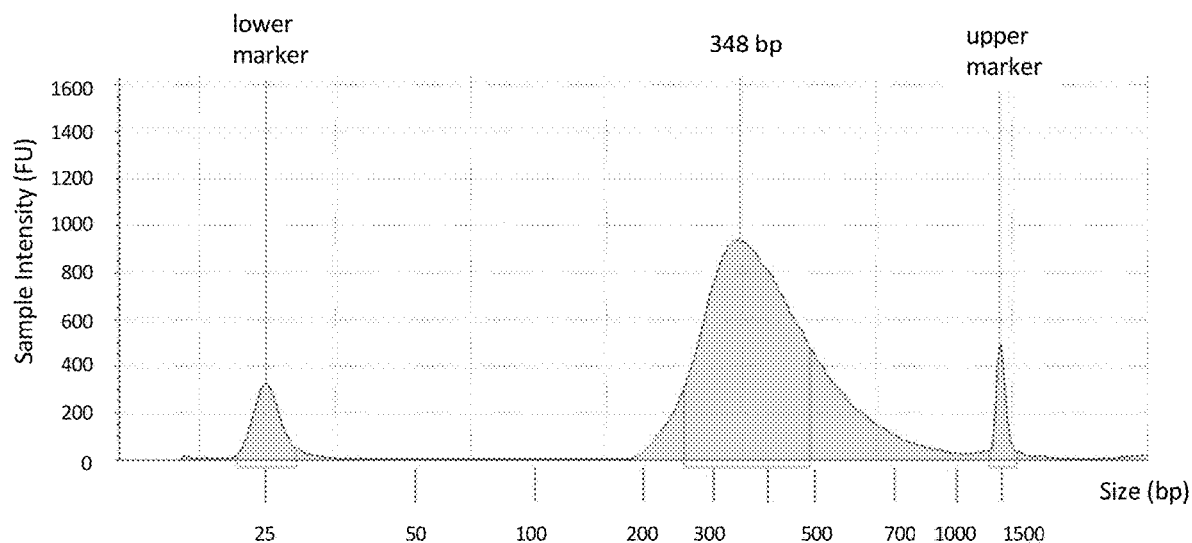
FIG. 3 shows that the protocol of FIG. 1 has been completed. The electropherogram (TapeStation®, Agilent, Santa Clara, Calif.) shows a peak at 348 bp that corresponds to the range of sizes and relative amounts of target and adaptors that make up the amplification products (see step 7 in FIG. 1) starting from a low input (high sensitivity) target in the polynucleotide sample.

The PCR products obtained from the target sequences were analyzed on an Agilent TapeStation and then sequenced using conventional methods. The Agilent TapeStation performs capillary electrophoresis and determines size and concentration of DNA fragments. Example results obtained from the TapeStation are shown in FIG. 3. As can be seen in FIG. 3, the amplified library contains DNA fragments with an average size of around 410 bp. The concentration was about 20 pM.

The table below shows example sequencing metrics for a low input target enrichment library made by the method described above. This data was produced using 50 ng input and a 30kb panel with paired end reads of 75 bp each.

| Low input library | Sample 1 |
| --- | --- |
| PF reads | 20,003,888 |
| % Aligned | 98.4% |
| % Inserts On Target | 90.9% |
| Mean Target Coverage (post duplicate filtering) | 10917.6 |
| Median Insert Size (bp) | 164 |

The following definitions explain the entries in the first column of this table:

Pass Filter (PF) Reads: The number of passing filter reads, including all reads marked as duplicates, identified as adaptor sequences, etc.;

% Aligned: The percentage of passing filter reads that were aligned at any quality and for at least one base, to the reference genome;

% Inserts On Target: The percentage of aligned inserts or templates, or in the case of single-end sequencing reads, that have at least one base overlapping at a target (post de-duplication);

Mean Target Coverage: the mean coverage in de-duplicated bases of all targets deemed to have received non-zero coverage where that is defined as any target with at least one base covered to 2×; and Median Insert Size: The median of the calculated insert size from all read-pairs that have both ends mapped to the same chromosome (post-deduplication).

In this example, deduplication was achieved by duplicate filtering. This data shown in the above table demonstrates the present method is capable of generating at least 10,000× mean target coverage with a high percentage (e.g., over 90%) of on-target inserts.

An explanation of duplication and deduplication is provided by Marx, Nature Methods 2017, 14, 473-476. Deduplication tools are offered by the Brabaham Institute UK, 10XGenomics and Joint Genome Institute (Dedupe).

Example 2

An Enriched Library of Target Sequences from 96 Tomato DNA Samples Following Pooling Materials and Methods The materials and methods from Example 1 were used up to and including the step of adaptor ligation and sample tagging (step 2 in FIG. 2) except that the adaptor was designed so that the top strand and not the bottom the strand contained the tag.

Tomato gDNA was analyzed. The double-stranded adaptor (first adaptor) had the following sequence, with the plus strand being 5'

```
                                              (SEQ ID NO: 3)
AATGATACGGCGACCACCGAGATCTACACCGAATACGNNNNNNNNN

NNNACACTCTTTCCCTACACGACGCTCTTCCGATCT 3'.
```

After step 2 of FIG. 2, the ligation was stopped by addition of 500 mM EDTA and mixing thoroughly. The samples were pooled together (step 3 of FIG. 2). The fragments were purified as described in Example 1.

Purified DNA fragments were hybridized to target isolation probes, each comprising a target-specific oligonucleotide linked to Biotin as described in Example 1. As in Example 1, one target-specific oligonucleotide was designed to bind the 5' and the other was designed to bind the 3' end of the target region. The remaining steps were the same as in Example 1.

Results

Figure 4:
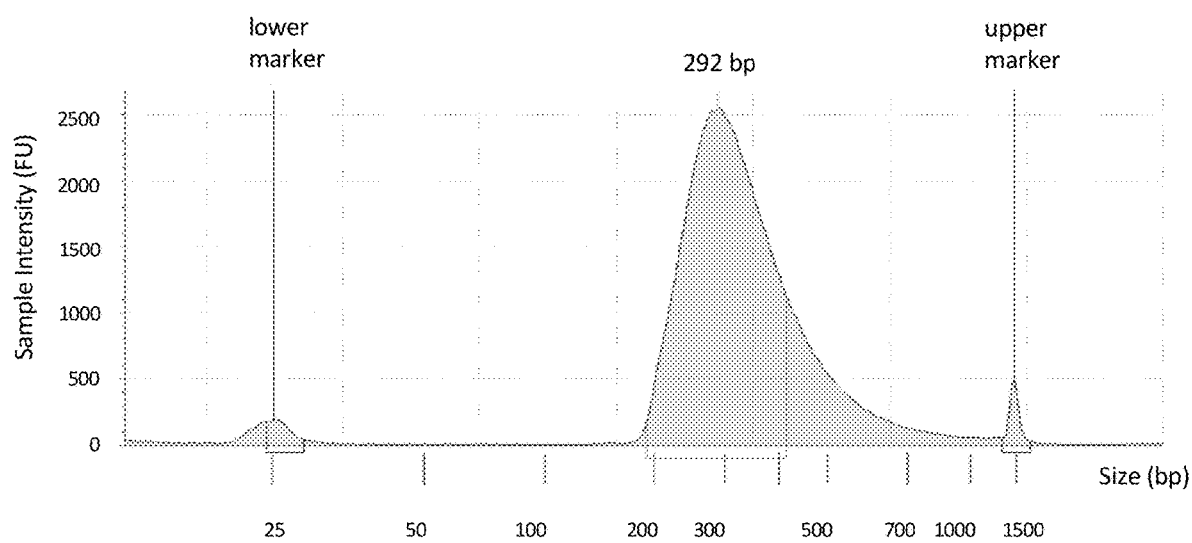
FIG. 4 shows that the protocol of FIG. 2 has been completed. The electropherogram (TapeStation) shows a peak at 292 bp that corresponds to the range of sizes and relative amounts of target and adaptors that make up the amplification products (see step 7 in FIG. 2) starting from a genotyping target in the polynucleotide sample.

The PCR products obtained from the target sequences were analyzed on an Agilent TapeStation and then sequenced using conventional methods. The TapeStation performs capillary electrophoresis and determines size and concentration of DNA fragments. Exemplary results obtained from the TapeStation are shown in FIG. 4. As can be seen in FIG. 4, the amplified library contains DNA fragments with an average size of around 350 bp. The concentration is around 13400 pg/μL.

The table below shows exemplary sequencing metrics for a target enrichment library made by the method described above. In this example, 96 tomato samples were fragmented independently, tagged with a unique sample tag in the adaptor, then pooled together in a single hybridization (i.e. the samples were multiplexed). The samples could be discriminated from one another in the analysis of the sequencing data by using the unique sample tags to find the sequencing reads that correspond to each sample (i.e. the samples were de-multiplexed).

This representative data from a single sample was produced using 25 ng tomato DNA input and a panel covering 2323 genomic markers (single nucleotide polymorphisms, or SNPs) with paired end reads of 75 bp each. Additional data from all 96 samples in this example may be seen in FIG. 4.

| Single sample from a 96 plex hybridization | Sample 1 |
|---|---|
| PF reads | 1,614,772 |
| % Aligned | 99.25% |
| % Inserts On Target | 84.02% |
| Mean Target Coverage (post duplicate filtering) | 65.58 |
| Median Insert Size (bp) | 116 |

This data shown in the above table and in FIG. 4 demonstrates the present method is capable of generating at least 50× mean target coverage with a high percentage (e.g., over 80%) of on-target inserts with 96 samples participating in a single hybridization reaction.

Example 3

Analysis of a SNP in Tomato Plants

A single leaf punch from each of 96 individual tomato plants (e.g., all of a single variety of interest) was placed in each well of a 96 well plate for subsequent DNA extraction. Following DNA extraction, fragmentation, and adaptor ligation and enrichment described in Example 2 (steps 1-3), the 5' adaptor ligated fragments of the samples in the 96 wells were pooled in a single hybridization mix containing oligonucleotide with affinity binding domains. Steps 4-7 in FIG. 2 were completed and then combined with pooled samples from multiple other 96 well plates similarly treated. For example, 96 hybridizations may be performed in parallel, each comprising multiplexed tagged fragments from 96 plants (96 plants/well X 96 wells=9,216 plants on one hybridization plate). The products of these 96 hybridization reactions were pooled together (i.e. multiplexed) in a single sequencing reaction.

What is claimed is:

1. A method for enriching for target sequences in biological samples, each sample characterized by a genome, the method comprising:
   (a) obtaining duplex polynucleotide fragments from the genomes of each of the biological samples;
   (b) ligating a first adaptor to the fragments from each sample to produce ligated polynucleotide fragments wherein each sample is in a separate reaction mix and wherein the first adaptor comprises:
   a 5' top strand that comprises from 5' to 3', a leader sequence, a sample tag, and a sequence that is complementary to a 3' bottom strand, the 3' bottom strand comprising at least one modified nucleotide and not the sample tag nor the leader sequence, wherein at least some of the polynucleotide fragments in each sample comprise a target sequence;
   (c) pooling the ligated polynucleotide fragments into a single reaction mix wherein each sample of the multiple samples is tagged with a different sample tag;
   (d) hybridizing an oligonucleotide having an affinity binding domain to the 3' end of the target sequence on each strand of the pooled polynucleotide fragments and immobilizing the hybridized oligonucleotide on a substrate;
   (e) removing any 3' non-target single stranded overhang sequences to form a double-stranded end of the polynucleotide fragment;
   (f) ligating a second adaptor, optionally having an index sequence, to the 3' double-stranded end of the polynucleotide fragment, wherein:
      (i) the second adaptor has a duplex at its 5' end and a 3' single strand overhang with a terminal 3'-5' exonuclease blocking moiety on its 3' end; and
      (ii) the duplex 5' end has a top strand and a bottom strand where the bottom strand has at least one modified nucleotide;
   (g) removing the bottom strand of the second adaptor by enzymatic degradation at the modified nucleotides to form a single stranded polynucleotide immobilized on a substrate by the hybridized oligonucleotide;
   (h) removing immobilized polynucleotides that do not contain target sequences using a 3'-5' double-stranded exonuclease; and
   (i) obtaining the enriched target sequences.

2. The method according to claim 1, further comprising: introducing the index sequence during library amplification.

3. The method according to claim 2, further comprising pooling the polynucleotides having the index sequence with other polynucleotides having different index sequences.

4. The method according to claim 3, wherein step (i) further comprises sequencing the enriched target sequences in a single sequencing reaction to determine the genotype of the biological samples.

5. The method according to claim 1, wherein step (e) further comprises using a 3'-5' single stranded exonuclease or a plurality of 3'-5' single stranded exonucleases to remove the 3' non target single stranded region.

6. The method according to claim 1, wherein the 5' top strand in (b) further comprises a unique molecule identifier (UMI).

7. The method according to claim 1, wherein the at least one modified nucleotide in (b) and (f) are deoxyuridine and enzyme degradation in (e) and (g) is achieved using UDG.

8. The method according to claim 1, wherein (g) further comprises amplifying the immobilized polynucleotides using a primer containing an index sequence.

9. The method according to claim 1, wherein step (i) further comprises sequencing the enriched target sequences in the biological samples in a single sequencing step.

10. The method according to claim 9 further comprising obtaining genotypes from the sequencing data.

11. The method according to claim 1, wherein the duplex polynucleotide fragments comprise DNA.

12. The method according to claim 1, wherein the affinity binding domain is biotin.

13. A method of making an enriched population of polynucleotides comprising target sequences from biological samples, each sample characterized by a genome, the method comprising:
(a) A-tailing duplex polynucleotide fragments from the genomes of the biological samples to produce A-tailed polynucleotide fragments;
(b) ligating a first adaptor to the A-tailed polynucleotide fragments from each sample to produce ligated polynucleotide fragments wherein each sample is in a separate reaction mix and wherein the first adaptor comprises:
a 5' top strand that comprises from 5' to 3', a leader sequence, a sample tag unique to each separate reaction mix, and a sequence that is complementary to a 3' bottom strand, the 3' bottom strand comprising at least one modified nucleotide and not the sample tag nor the leader sequence,
wherein at least some of the polynucleotide fragments in each sample comprise a target sequence;
(c) pooling the ligated polynucleotide fragments into a single reaction mix to form pooled polynucleotide fragments;
(d) hybridizing an oligonucleotide having an affinity binding domain to the 3' end of the target sequence on each strand of the pooled polynucleotide fragments to form duplexes, each duplex comprising one of the pooled polynucleotide fragments, and immobilizing the duplexes on a substrate to form immobilized duplexes;
(e) removing from the immobilized duplexes any 3' non-target single stranded overhanging sequences to form a polynucleotide-oligonucleotide duplex having a double-stranded end;
(f) ligating a second adaptor, optionally having an index sequence, to the double-stranded end of the polynucleotide-oligonucleotide duplexes to form second adapter ligation products, wherein:
(i) the second adaptor has a duplex at its 5' end and a 3' single strand overhang with a terminal 3'-5' exonuclease blocking moiety on its 3' end; and
(ii) the duplex 5' end has a top strand and a bottom strand where the bottom strand has at least one modified nucleotide;
(g) enzymatically degrading the modified nucleotides of the second adaptor ligation products to form a single stranded polynucleotide immobilized on a substrate by the hybridized oligonucleotide; and
(h) removing immobilized polynucleotides that do not contain target sequences using a 3'-5' double-stranded exonuclease to form the enriched population of single stranded polynucleotides comprising target sequences.

14. The method according to claim 13 further comprising contacting the single stranded polynucleotides with one or more primers to amplify the enriched target sequences.

15. The method according to claim 13, further comprising: introducing the index sequence during library amplification.

16. The method according to claim 13, wherein step (e) further comprises using a 3'-5' single stranded exonuclease or a plurality of 3'-5' single stranded exonucleases to remove the 3' non target single stranded region.

17. The method according to claim 13, wherein the 5' top strand in (b) further comprises a unique molecule identifier (UMI).

18. The method according to claim 13, wherein the at least one modified nucleotide in (b) and (f) are deoxyuridine and enzyme degradation in (e) and (g) is achieved using UDG.

19. The method according to claim 13, wherein (g) further comprises amplifying the immobilized polynucleotides using a primer containing an index sequence.

20. The method according to claim 13, further comprising pooling the polynucleotides having the index sequence with other polynucleotides having different index sequences.

21. The method according to claim 20, wherein step (h) further comprises sequencing in a single sequencing reaction the enriched population of single stranded polynucleotides comprising target sequences to determine the genotype of the biological samples.

22. The method according to claim 13, wherein step (h) further comprises sequencing in a single sequencing step the enriched population of single stranded polynucleotides comprising target sequences.

23. The method according to claim 22 further comprising obtaining genotypes from the sequencing data.

24. The method according to claim 13, wherein the affinity binding domain is biotin.

* * * * *

SEQUENCE LISTING

```
<160> NUMBER OF SEQ ID NOS: 4

<210> SEQ ID NO 1
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (33)..(44)
<223> OTHER INFORMATION: n is a, c, g, or t

<400> SEQUENCE: 1
gatcggaaga gcgtcgtgta gggaaagagt gtnnnnnnnn nnnnaggcta tagtgtagat    60
```

```
ctcggtggtc gccgtatcat t                                                    81

<210> SEQ ID NO 2
<211> LENGTH: 18
<212> TYPE: DNA
<213> ORGANISM: Artificial Sequence
<220> FEATURE:
<223> OTHER INFORMATION: Synthetic construct

<400> SEQUENCE: 2
aatgatacgg cgaccacc                                                        18

<210> SEQ ID NO 3
<211> LENGTH: 82
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (38)..(49)
<223> OTHER INFORMATION: n is a, c, g, or t

<400> SEQUENCE: 3
aatgatacgg cgaccaccga gatctacacc gaatacgnnn nnnnnnnna cactctttcc           60 ctacacgacg ctcttccgat ct                                                   82

<210> SEQ ID NO 4
<211> LENGTH: 34
<212> TYPE: DNA
<213> ORGANISM: Artificial Sequence
<220> FEATURE:
<223> OTHER INFORMATION: Synthetic construct

<400> SEQUENCE: 4
agatcggaag agcacacgtc tgaactccag tcac                                      34
```